United States Patent [19]

Anis

[11] Patent Number: 4,963,149
[45] Date of Patent: Oct. 16, 1990

[54] FLEXIBLE ONE-PIECE POSTERIOR CHAMBER LENS AND METHOD OF IMPLANTING THE SAME

[76] Inventor: Aziz Y. Anis, 7531 N. Hampton, Lincoln, Nebr. 68506

[21] Appl. No.: 317,069

[22] Filed: Feb. 23, 1989

Related U.S. Application Data

[63] Continuation of Ser. No. 79,509, Jul. 30, 1987, abandoned, and a continuation-in-part of Ser. No. 201,388, May 17, 1988, Pat. No. 4,880,427, which is a continuation of Ser. No. 624,232, Jun. 25, 1984, abandoned.

[51] Int. Cl.⁵ ............................................. A61F 2/16
[52] U.S. Cl. ....................................................... 623/6
[58] Field of Search ........................................ 623/6, 5

[56] References Cited

U.S. PATENT DOCUMENTS 2,754,520  7/1956  Crawford, Jr. .................... 623/5
4,280,232  7/1981  Hummel ............................. 623/6
4,681,586  7/1987  Woods ............................... 623/6

FOREIGN PATENT DOCUMENTS 8500527   1/1986  Netherlands ...................... 623/6
2124500A  2/1984  United Kingdom ............... 623/6

Primary Examiner—Ronald Frinks
Attorney, Agent, or Firm—Vincent L. Carney

[57] ABSTRACT

An intraocular lens implant comprising a flexible, substantially ring-shaped position fixation member having a lens body positioned centrally therein. The lens body is connected to the position fixation member by either rim portions or posts which have a notch formed therein for receiving one end of the incision through which the implant will be inserted. The notch permits the implant to be inserted in an incision shorter than the diameter of the implant. The method of implanting the implant is also described.

5 Claims, 3 Drawing Sheets

FLEXIBLE ONE-PIECE POSTERIOR CHAMBER LENS AND METHOD OF IMPLANTING THE SAME

RELATED APPLICATIONS

This application is a continuation of application Ser. No. 079,509 filed July 30, 1987, now abandoned, and a continuation-in-part of application Ser. No. 201,388 filed May 17, 1988 for FLEXIBLE POSTERIOR CHAMBER LENS, now U.S. Pat. No. 4,880,427 which in turn is a continuation of application Ser. No. 624,232 filed June 25, 1984, now abandoned.

BACKGROUND OF THE INVENTION

This invention relates to a posterior chamber lens.

The human eye is a very complex organ comprising numerous interacting elements which gather, focus, and transmit light rays to nerve endings which eventually transmit the information to the brain for image perception. The eye includes a natural crystalline lens of avascular tissue, the transparency of which depends upon the critical regularity of its fibers and the balance of its chemical constituents. Obviously, there are enumerable factors which may interfere with lens makeup and thereby affect its transparent character. No matter what the reason, a condition of opacity in the lens, commonly called cataract, reduces the visual performance of the eye. When the visual performance is reduced to an unacceptable level, surgical cataract extraction becomes a necessity.

An eye without a lens, a condition called aphakia, is obviously defective from an optical point of view in as much as it cannot properly refract incident light rays. Aphakic correction may be accomplished in three ways:

(1) thick eye glasses worn in front of the eye;
(2) contact lenses worn on the eye, or
(3) artificial intraocular lens implant within the eye.

It is this latter procedure with which the instant invention is concerned.

The structure and procedure of installing an intraocular lens is very critical because of the elements which make up the eye are extremely sensitive and subject to irreparable damage. Numerous experimental lens designs have been abandoned through the years because they caused corneal damage and other manifestations of intraocular irritation. For example, in the late 1940's and early 1950's, H. Ridley conducted clinical experiments with an artificial intraocular lens which included a lens portion having foot-like projections extending radially away therefrom. This device was placed in the posterior chamber with the feet extending between the ciliary processes and the base of the iris. The lens proved positionally unstable and resulted in unsatisfactory amounts of irritation.

Many attempts have been made to provide a satisfactory intraocular lens. In an effort to remedy the problems associated with the prior art lens implants, applicant previously has been granted U.S. Pat. Nos. 4,143,427; 4,166,293; 4,251,887 and 4,575,374.

Although applicant's previous lens implants did represent a significant advance in the art, it is believed that the instant invention represents a further advance in the art in that it permits a lens to be implanted with a minimal incision being required.

Therefore, it is a principal object of this invention to provide an improved posterior chamber lens.

A further object of the invention is to provide an improved posterior chamber lens which is designed so that it may be inserted into the eye through a shorter incision than previously possible.

A further object of the invention is to provide a posterior chamber lens including substantially ring-shaped member which extends around a centrally positioned lens body with the ring-shaped member being compressible towards the lens body to facilitate the insertion of the implant into the eye.

Yet another object of the invention is to provide a lens of the type described which is of one-piece construction.

Still another object of the invention is to provide a posterior chamber lens which will remain in place even if pressure or force is inadvertently applied to one portion of the lens.

These and other objects will be apparent to those skilled in the art.

SUMMARY OF THE INVENTION

Figure 1:
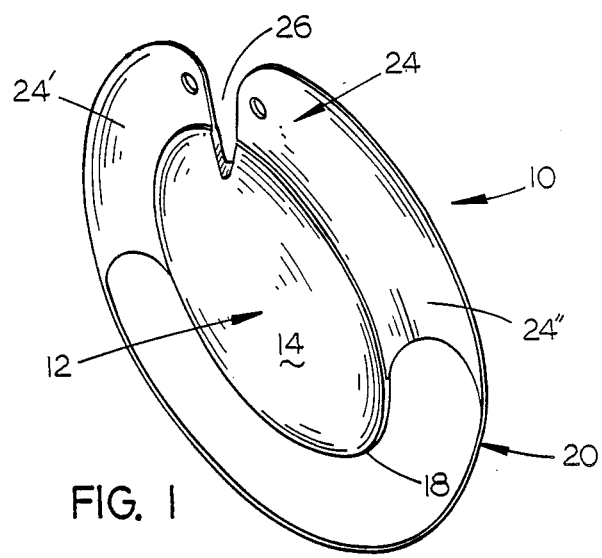
FIG. 1 is a perspective view of the lens of this invention.

A posterior chamber lens implant is described which may be implanted in the eye after the natural lens of the eye has been removed. The lens implant comprises a flexible, substantially ring-shaped position fixation member which extends around a lens body having a diameter less than the position fixation element. A cut-out portion or notch extends into the lens implant to facilitate the insertion of the implant into the eye through an incision During the installation, the lens implant is inserted into and through the incision so that the notch "receives" one end of the incision so that the lens implant may be inserted through a shorter incision than normally possible. Once the implant has been so positioned, the implant is rotated about the notch to position the implant within the eye. A portion of the position fixation member can be compressed towards the lens body to enable the implant to be properly positioned. When positioned within the eye, there is a substantially 360° engagement of the lens with the eye to positively maintain the lens implant in position.

DESCRIPTION OF THE PREFERRED EMBODIMENT

The lens implant of this invention is referred to generally by the reference numeral 10. Lens implant 10 includes a disc-shaped lens body 12 which may either be of the convex-plano or convex-convex or other conventional configuration as desired. For purposes of description, lens body 12 will be described as having a front or anterior face 14, back or posterior face 16 and peripheral edge 18.

Figure 2:
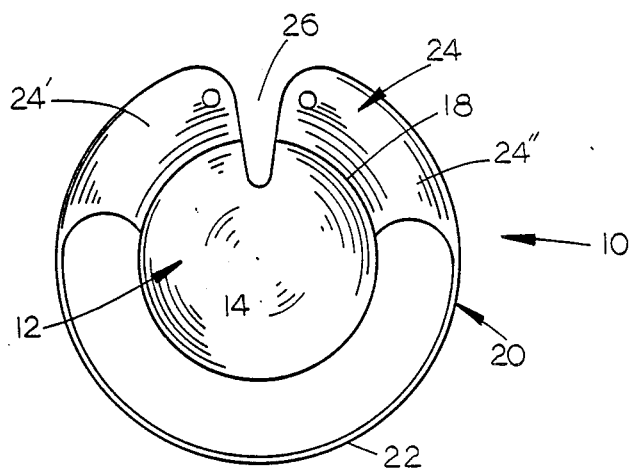
FIG. 2 is an elevational view of the invention.
Figure 3:
FIG. 3 is an end view of a modified form of the invention.
Figure 4:
FIG. 4 is an end view of a still further modified form of the invention.
Figure 5:
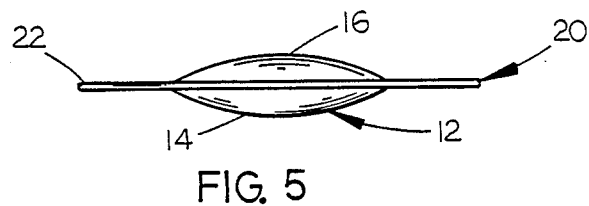
FIG. 5 is an end view of the embodiment of FIG. 2.

A ring-shaped position fixation member 20 is positioned outwardly of the lens body 12 as illustrated in the drawings. As seen, fixation member 20 includes a loop portion 22 which extends from rim portion 24. Rim portion 24 is provided with a notch or recess 26 formed therein which extends thereinto as seen in the drawings to define rim portions 24' and 24". As seen in FIGS. 1 and 2, the inner end of the recess 26 extends into the lens body 12.

Figure 6:
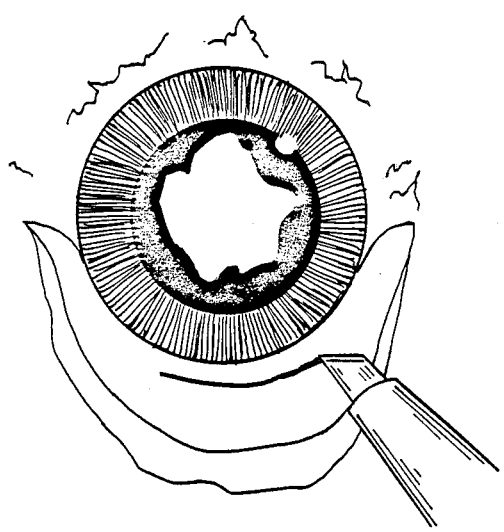
FIG. 6 is a plan view illustrating an incision being created during the implantation process.
Figure 7:
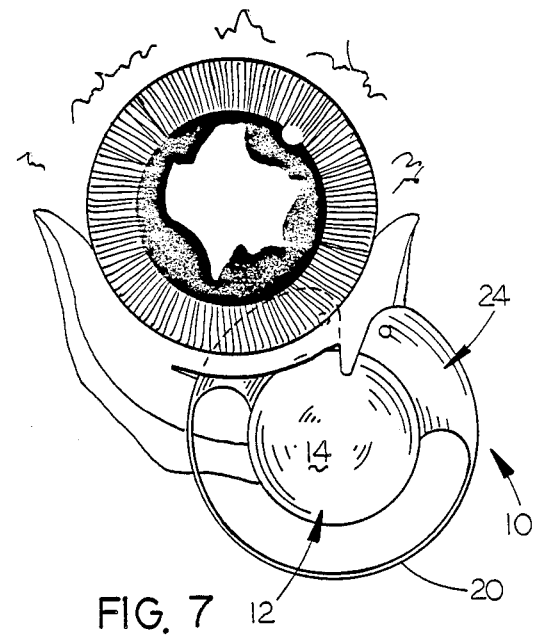
FIG. 7 is a view similar to FIG. 6 but which illustrates the implant being implanted.
Figure 8:
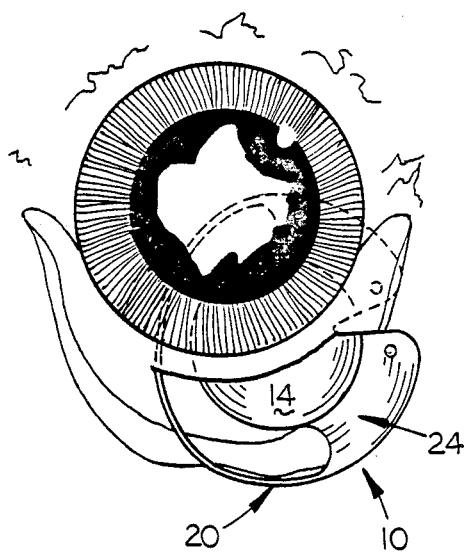
FIG. 8 is a view similar to FIGS. 6 and 7 but which illustrates the lens being further implanted.
Figure 9:
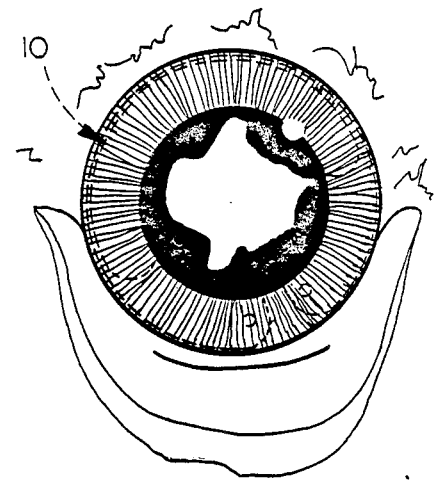
FIG. 9 is a view illustrating the lens implant after it has been implanted.

The lens implant of this invention is inserted or implanted as follows. As seen in FIG. 6, an incision is created with the incision being shorter than would normally be required As seen in FIG. 7, the implant is inserted into the incision so that the notch 26 receives one end of the incision which permits the implant to be implanted through a shorter incision than normally required. The implant 10 is rotated or pivoted about that end of the incision which is received by the notch 26 and the implant 10 is pivoted or rotated utilizing the one end of the incision as a fulcrum or pivot point. As the lens implant 10 is rotated from the position of FIG. 7 to the position of FIG. 8, the fixation member 20 is compressed as illustrated in FIG. 8. Rotation of the lens implant is continued until the entire implant is received within the capsular bag. FIG. 9 illustrates the lens implant in its implanted condition.

Figure 10:
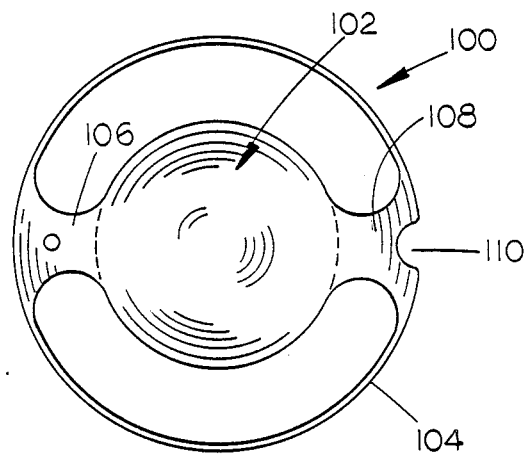
FIG. 10 is an elevational view of a modified form of the invention.

FIG. 10 illustrates a modification of the invention and is referred to generally by the reference numeral 100. Lens implant 100 includes a disc-shaped lens body 102 which may bed of a convex-plano, convex-convex, or any other convenient configuration. Lens implant 100 is provided with a ring-shaped position fixation member 104 extending therearound which is connected to the lens body 102 by a pair of opposed posts 106 and 108 as illustrated in FIG. 10. Preferably, lens body 102 has a diameter of 6 millimeters but the same can be between 4.0 and 8.0 millimeters. Preferably, the diameter of fixation member 104 is 10.5 millimeters but the same can vary between 8.0 millimeters and 13.0 millimeters. The lens implant is provided with a notch 110 which extends into post 108 although the notch 110 could extend into the post 106 if desired. Notch 110 performs the same function as notch 26 is the embodiment described in FIGS. 1-9. During implantation, notch 110 in implant 100 would receive one end of the incision in an identical fashion to that just described.

Thus it can be seen that a novel lens implant has been provided which enables the implant to be inserted through a shorter incision than normally required due to the fact that the notch 26 or notch 110 is provided and is adapted to receive one end of the incision as previously described.

The substantially 360° engagement of the lens implant with the interior of the eye ensures that the implant will remain in position even if accidentally jarred or struck. Thus it can be seen that the implant of this invention accomplishes at least all of its stated objectives.

I claim:

1. An intraocular lens implant, comprising:
   a flexible, substantially ring-shaped position fixation member;
   a lens body having a diameter less than said position fixation member and being positioned within said position fixation member; and
   connection means connecting said lens body with said position fixation member;
   said position fixation member, lens body and said connection means being of one-piece construction;
   said position fixation member and connection means providing a substantially 360 degrees of contact with an eye interior and having a notch formed therein which extends inwardly thereinto for receiving one end of the incision through which the implant will be inserted;
   said connection means including at least one rim portion and said position fixation member being a loop member connected to said lens by said connection means;
   said loop portion being located to permit compression during insertion whereby the notch and compressed loop portion reduce the size of incision needed for insertion of the lens implant into an eye.

2. The implant of claim 1 wherein said notch is substantially V-shaped.

3. An intraocular lens implant, comprising:
   a flexible, substantially ring-shaped position fixation member;
   a lens body having a diameter less than said position fixation member and being positioned within said position fixation member; and
   connection means connecting said lens body with said position fixation member;
   said position fixation member, lens body and said connection means being of one-piece construction;
   said position fixation member and connection means providing a substantially 360 degrees of contact with an eye interior and having a notch formed therein which extends inwardly thereinto for receiving one end of the incision through which the implant will be inserted;
   said connection means including at least one rim portion and said position fixation member being a loop member connected to said lens by said connection means;
   said loop portion being located to permit compression during insertion whereby the notch and compressed loop portion reduces the size of incision needed for insertion of the lens implant into an eye;
   said connection means comprising at least one post member which extends oppositely from said lens body to said position fixation member, said at least one post member having said notch formed therein.

4. The method of implanting a lens implant through an incision in an eye, comprising the steps of:
   providing a lens implant including a substantially ring-shaped position fixation member which has a notch formed therein which extends radially inwardly from the periphery thereof;
   positioning the lens implant with respect to the incision so that the notch receives the one end of the incision;
   rotating the lens implant with respect to the eye and the incision whereby the lens implant is rotated about the end of the incision, with the end of the incision serving as a fulcrum until the implant has been implanted within the eye; and
   compressing said fixation member during rotation of the lens implant.

5. The method of claim 4 further including the step of making an incision in the eye that is shorter than normally needed for an implant.

* * * * *